(12) United States Patent
Fiedler et al.

(10) Patent No.: US 10,918,759 B2
(45) Date of Patent: Feb. 16, 2021

(54) AIR PURIFICATION DEVICE

(71) Applicant: DR. SCHNEIDER KUNSTSTOFFWERKE GMBH, Kronach (DE)

(72) Inventors: Jochen Fiedler, Pressig (DE); Gerhard Endres, Mainleus (DE)

(73) Assignee: DR. SCHNEIDER KUNSTSTOFFWERKE GMBH

( * ) Notice: Subject to any disclaimer, the term of this patent is extended or adjusted under 35 U.S.C. 154(b) by 228 days.

(21) Appl. No.: 16/061,308

(22) PCT Filed: Mar. 20, 2017

(86) PCT No.: PCT/EP2017/056537
§ 371 (c)(1),
(2) Date: Jun. 11, 2018

(87) PCT Pub. No.: WO2017/162577
PCT Pub. Date: Sep. 28, 2017

(65) Prior Publication Data
US 2019/0001015 A1   Jan. 3, 2019

(30) Foreign Application Priority Data
Mar. 22, 2016   (DE) .................... 10 2016 105 276.0

(51) Int. Cl.
*A61L 9/20* (2006.01)
*B60H 3/06* (2006.01)
(Continued)

(52) U.S. Cl.
CPC ............ *A61L 9/205* (2013.01); *B01D 53/007* (2013.01); *B01D 53/885* (2013.01); *B01J 21/063* (2013.01);
(Continued)

(58) Field of Classification Search
CPC ............... A61L 9/205; A61L 2209/12; A61L 2209/111; B01D 53/007; B01D 53/885;
(Continued)

(56) References Cited

U.S. PATENT DOCUMENTS 5,919,422 A    7/1999  Yamanaka et al.
6,342,128 B1 * 1/2002  Tabatabaie-Raissi ..................
                                                B01D 53/885
                                                   204/157.15

(Continued)

FOREIGN PATENT DOCUMENTS

DE          10084820      12/2002
DE       202007019288      4/2012
(Continued)

OTHER PUBLICATIONS

German Office Action (w/machine translation) issued in application No. 10 2016 105 276.0, dated Apr. 5, 2017 (14 pgs).
(Continued)

*Primary Examiner* — Regina M Yoo
(74) *Attorney, Agent, or Firm* — Hayes Soloway P.C.

(57) ABSTRACT

An air purification unit has a housing which has at least one inlet opening for delivering an air stream and at least one outlet opening for discharging the air stream delivered via the inlet opening. At least one air purification unit and at least one lighting unit are arranged in the housing, wherein the at least one air purification unit and the at least one lighting unit are arranged opposite one another in the housing. The at least one air purification unit has at least one photocatalytically active surface region. The air stream is guided in the housing at least partially along the at least one photocatalytically active surface region of the at least one air
(Continued)

purification unit, wherein the surface region is at least partially coated with titanium dioxide or doped with titanium dioxide ions ions.

18 Claims, 8 Drawing Sheets

(51) Int. Cl.
*B01D 53/88* (2006.01)
*B01D 53/00* (2006.01)
*B01J 21/06* (2006.01)
*B01J 35/00* (2006.01)

(52) U.S. Cl.
CPC .......... *B01J 35/004* (2013.01); *B60H 3/0608* (2013.01); *A61L 2209/111* (2013.01); *A61L 2209/12* (2013.01); *B01D 2255/20707* (2013.01); *B01D 2255/802* (2013.01); *B01D 2257/708* (2013.01); *B01D 2259/4566* (2013.01); *B01D 2259/804* (2013.01); *B60H 2003/0675* (2013.01)

(58) Field of Classification Search
CPC ...... B01D 2259/804; B01D 2259/4566; B01D 2257/708; B01D 2255/20707; B01D 2255/802; B01J 21/063; B01J 35/004; B60H 3/0608; B60H 2003/0675
See application file for complete search history.

(56) References Cited

U.S. PATENT DOCUMENTS

| | | | | |
|---|---|---|---|---|
| 6,562,309 | B2* | 5/2003 | Burke ................. | B01D 53/885 204/157.3 |
| 6,797,127 | B1 | 9/2004 | Murata et al. | |
| 7,063,820 | B2* | 6/2006 | Goswami ................. | A61L 2/02 422/186.3 |
| 9,586,460 | B2 | 3/2017 | Gross et al. | |
| 9,867,897 | B2* | 1/2018 | Eide ....................... | A61L 9/205 |
| 9,868,129 | B2* | 1/2018 | Hayden ................. | C02F 1/325 |
| 10,293,072 | B2* | 5/2019 | Taghipour ........... | B01D 53/8668 |
| 10,517,980 | B2* | 12/2019 | Kim ...................... | A61L 9/205 |
| 2003/0150707 | A1* | 8/2003 | Carmignani ........... | B01J 35/002 204/157.3 |
| 2005/0224335 | A1* | 10/2005 | Carmignani ......... | B01J 19/2495 204/157.15 |
| 2007/0101867 | A1* | 5/2007 | Hunter ................. | A61L 9/205 96/224 |
| 2007/0253860 | A1* | 11/2007 | Schroder ................. | A61L 9/205 422/4 |
| 2010/0209312 | A1* | 8/2010 | Pastor ..................... | A61L 9/205 422/186.3 |
| 2010/0260644 | A1* | 10/2010 | Day ........................ | A61L 9/205 422/121 |
| 2012/0128539 | A1* | 5/2012 | Gross ...................... | A61L 9/205 422/121 |
| 2012/0228236 | A1* | 9/2012 | Hawkins, II ........... | C02F 1/725 210/748.14 |
| 2013/0291735 | A1* | 11/2013 | Livchak ................... | A61L 9/20 96/224 |
| 2015/0064069 | A1* | 3/2015 | Yi ..................... | B01D 46/0028 422/121 |
| 2015/0231298 | A1* | 8/2015 | Eide .................... | B01D 53/885 422/122 |
| 2015/0359922 | A1* | 12/2015 | Kim ......................... | A61L 9/00 422/121 |
| 2016/0051719 | A1* | 2/2016 | Watanabe ............... | A61L 9/205 422/121 |
| 2016/0250372 | A1* | 9/2016 | Dytrych ................. | A61L 9/205 422/122 |
| 2016/0256590 | A1* | 9/2016 | Taghipour ............. | A61L 9/205 |
| 2017/0028820 | A1* | 2/2017 | Walsh .................. | B60H 3/0658 |
| 2017/0326264 | A1* | 11/2017 | Kim ....................... | B01D 53/04 |

FOREIGN PATENT DOCUMENTS

| | | |
|---|---|---|
| DE | 102014012870 | 3/2015 |
| EP | 0707989 | 4/1996 |
| EP | 2181720 | 5/2010 |
| EP | 2554583 | 2/2013 |
| JP | H11157332 | 6/1999 |
| JP | 2006312152 | 11/2006 |
| JP | 2013094736 | 5/2013 |
| WO | WO2005030371 | 4/2005 |
| WO | WO2010052001 | 5/2010 |
| WO | WO2016105224 | 6/2016 |

OTHER PUBLICATIONS

International Preliminary Report on Patentability (w/machine translation) issued in application No. PCT/EP2017/056537, dated Mar. 8, 2018 (14 pgs).

International Search Report (w/translation) and Written Opinion (no translation) issued in application No. PCT/EP2017/056537, dated Jun. 8, 2017 (13 pgs).

International Preliminary Report on Patentability (translation) issued in application No. PCT/EP2017/056537, dated Sep. 27, 2018 (7 pgs).

* cited by examiner

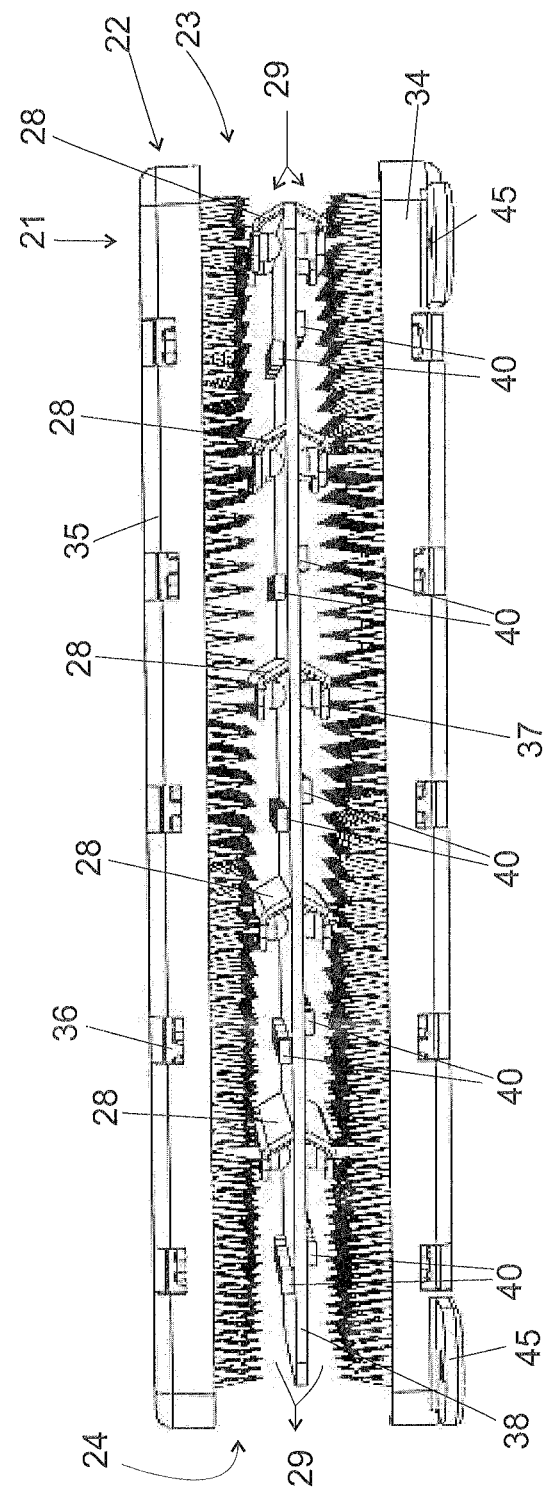

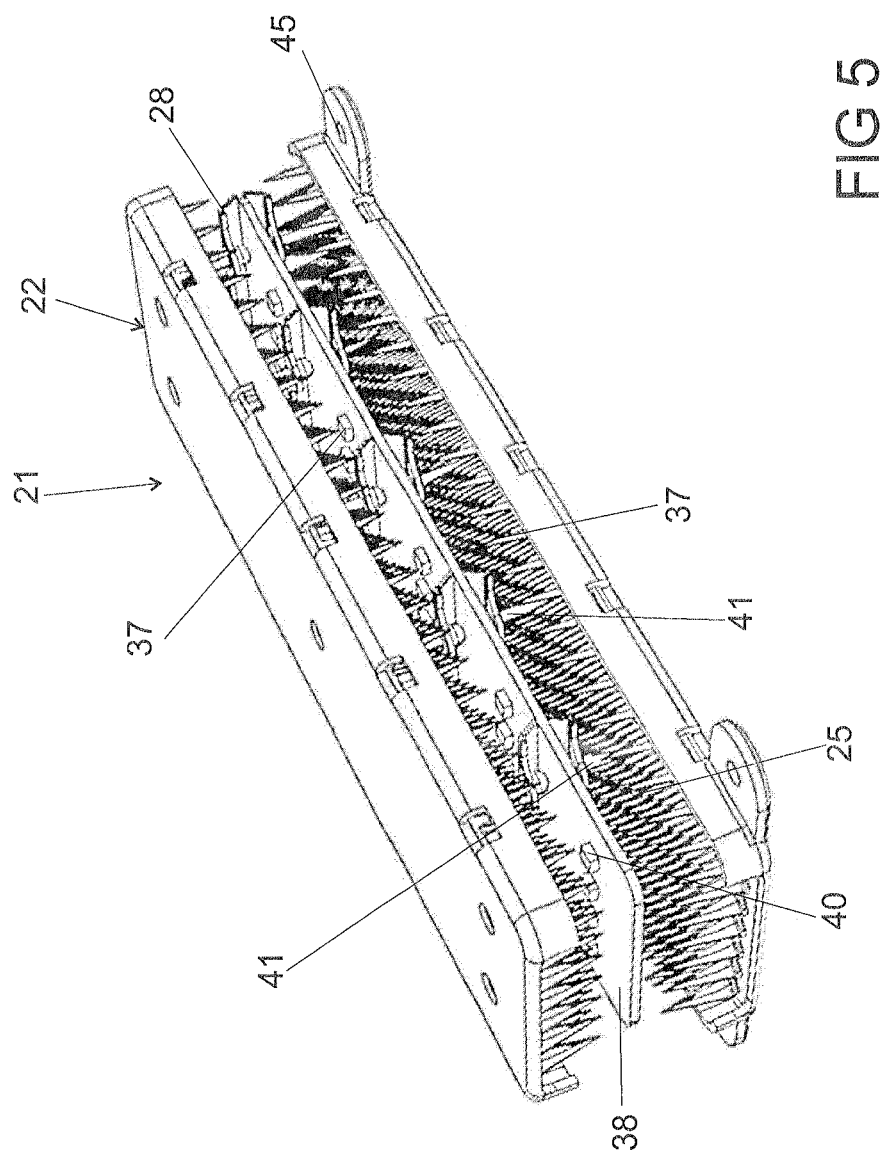

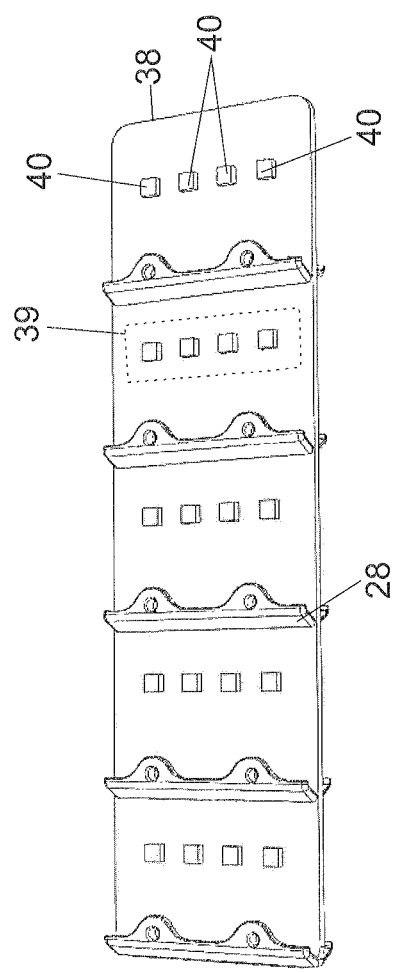

AIR PURIFICATION DEVICE

BACKGROUND OF THE INVENTION

The present equipment serves for purification of air, particularly for purification of air in motor vehicle interiors.

Various devices for air purification in motor vehicles are known from the prior art. These are mostly constructed and arranged in such a way that air is continuously extracted from the vehicle interior, conducted across a filter and then fed back to the vehicle interior.

Thus, an air purifier is known from DE 10 2014 012 870 A1. This air purifier uses ultraviolet radiation for air purification. The air purifier comprises a housing with a housing inlet and a housing outlet, a fan arranged in the interior of the housing adjacent to the air inlet, an ultraviolet light-emitting diode unit and a filter unit. The filter unit is arranged in the interior of the housing across the fan along a flow path of the air. A flow arrangement arranged in the interior of the housing between the fan and the filter unit is also present. The flow control arrangement then controls the air flow along the flow path of the air between the outlet of the fan and the filter unit. In that case, photocatalytic ultraviolet light-emitting diodes are employed for purifying the air.

A system for air purification with use of ozone and a ceramic porous catalyser is disclosed in DE 20 2007 019 288 U1. The system comprises a housing, at least one inlet and outlet, at least one photon source, a ceramic core and a fluid flow generating device, wherein the photon source is arranged upstream of the ceramic core.

A photocatalyser for deodorising, cleaning, sterilising and purifying water or air is disclosed in U.S. Pat. No. 5,919,422 A. This has a substrate on which a titanium oxide film is arranged. Also present is a light-emitting diode which is arranged near the titanium oxide film and which emits ultraviolet light with a wavelength of 360 to 400 nanometres and radiates it onto the titanium dioxide film.

A device with a UV-A radiation source is disclosed in EP 2 181 720 A1, which illuminates a surface of a carrier having a photocatalyser on a titanium oxide basis. The carrier is provided with an inner layer consisting of a metallic copper plate. The carrier is provided with a carbon inner layer and two outer layers, inclusive of the photocatalyser. An air circulation unit for producing movement of the air along the carrier is provided, so that the produced air flow passes through and across the carrier. The solid metallic compound is produced from bacteriostatic or antimycotic or bacteriocidal metals.

A device for purifying air is known from EP 0 707 989 A1. Purification is carried out in the manner that outside air is inducted by way of a housing and a fan arranged therein, is purified in a plurality of purification steps and is then supplied to the interior space of the vehicle. The fan or the drive of the fan is supplied with power by way of solar cells which are arranged in the vehicle and serve as energy sources.

It is disadvantageous with the aforesaid prior art that the purifying action and, in particular, the elimination of noxious particles or odoriferous particles from the air to be purified are not adequately possible or possible over a longer period of time without maintenance intervention. This is due to the fact on the one hand that use is usually made of a mechanical filter which after a relatively short period of time has already taken up such a quantity of particles that it has to be exchanged in order to maintain the original purifying capability. If regular exchange is not carried out, such a filter contributes more to contamination of the air than purification thereof. It must be known to most users of air conditioning installations that a contaminated filter makes a substantial contribution to odour nuisance in a motor vehicle.

Moreover, it is disadvantageous that a filter change is connected with relatively high costs since usually such a change can be carried out only in a specialised workshop.

Moreover, it has to be taken into consideration that, in particular, new vehicles for a specific period of time deliver volatile organic compounds (VOC) and other substances hazardous to health. No systems are known from the prior art in the past in order to avoid this as far as possible and without a burden on the occupants of a vehicle. Filter systems such as described in the introduction and also able to filter out such compounds are, in fact, present in the prior art, but the period of time over which these compounds remain in the vehicle is comparatively lengthy.

It is therefore an object of the present invention to eliminate the disadvantages of the prior art and to indicate an air purification device which selectively reduces volatile organic substances and substances hazardous to health as well as other air contaminants in the air in the vehicle interior space and additionally also avoids and eliminates unpleasant odours.

SUMMARY OF THE INVENTION

The present invention relates to an air purification device comprising a housing having at least one inlet opening for the supply of an air flow and at least one outlet opening for discharge of the air flow supplied by way of the inlet opening. At least one air purifying unit and at least one lighting unit are arranged in the housing, wherein the at least one air purifying unit and the at least one lighting unit are arranged in the housing to be opposite one another. The at least one air purifying unit has at least one photocatalytically active surface region. The air flow is guided in the housing at least partially along the at least one photocatalytically active surface region of the at least one air purifying unit, wherein the at least one photocatalytically active surface region of the at least one air purifying unit can be illuminated with light by the at least one lighting unit and the at least one photocatalytically active surface region is at least partly coated with titanium dioxide ($TiO_2$) or doped with titanium dioxide ions ($TiO_2$ ions).

The basis of the invention is the $TiO_2$ layer consisting of an inorganic layer which at the same time has a reflective effect. The active $TiO_2$ is thereby prevented from attacking and in a given case dissolving organic adhesive layers, in which case the energy of the light is at the same time more efficiently utilised and distributed.

It is provided that the at least one air purifying unit is arranged at one of the inner walls of the housing or that the at least one air purifying unit is arranged in the middle of the housing to run through this in a plane. Through the arrangement of the at least one air purifying unit at one of the inner walls of the housing it is possible to realise secure fastening and at the same time the air flow can be so guided in the housing that it is optimally adapted to the at least one air purifying unit. In the case of an arrangement in the middle of the housing, the at least one air purifying unit can be directly surrounded by the air flow flowing into the housing and a good level of cleaning performance is achieved.

Further, it is provided that the at least one lighting unit is arranged in the housing on one of the inner walls of the housing to be opposite the at least one air purifying unit or in the centre of the housing to pass through this in a plane. The lighting unit is obligatory, since the photocatalytic purification process takes place only through light, preferably ultraviolet light, incident on the at least one air purifying unit or the photocatalytically active surface regions thereof. Satisfactory illumination and thus supply of ultraviolet light are therefore possible by this arrangement of the at least one lighting unit opposite the at least one air purifying unit. The purifying effect is also capable of being produced with deep blue (visible light) and the invention is thus also possible with deep blue (visible light); however, a doped $TiO_2$ then has to be used.

Moreover, it is provided that the at least one lighting unit is so arranged in the housing to be opposite the at least one air purifying unit that the light emitted by the at least one lighting unit impinges almost entirely on the at least one air purifying unit.

In an advantageous embodiment of the invention it is provided that lens which focus the light emitted by the at least one lighting unit onto the at least one air purifying unit are arranged in front of the at least one lighting unit or that light reflectors or light-reflecting regions which reflect the light emitted by the at least one lighting unit in the direction of the at least one air purifying unit are arranged behind and/or near the at least one lighting unit. Particularly good focusing of the emitted light on the at least one air purifying unit is achieved by the arrangement of the lenses. It is achieved through the arrangement of light reflectors or light reflecting regions that even light which is not directed directly onto the at least one air purifying unit is nevertheless conducted at least partly to the air purifying unit.

In an advantageous embodiment of the invention it is provided that the inner walls of the housing (2, 22) are painted white or coated with a light-reflecting material. It is thereby achieved that the light emitted by the at least one lighting unit is not absorbed by the housing, but is reflected and thus additionally conducted to or in the direction of the at least one air purifying unit.

In an advantageous embodiment of the invention it is provided that the at least one lighting unit consists of at least one light-emitting diode which emits ultraviolet light. Activation by visible light can also take place depending on the doping of the photocatalyser.

In an advantageous embodiment of the invention it is provided that the at least one air purifying unit extends almost over the entire area of the housing base and/or the housing cover of the housing and is fixable to the housing base and/or housing cover. A large area can thus be employed for air purification and the at least one air purifying unit can be satisfactorily fixed in the housing.

It is provided that the at least one air purifying unit is shaped on the side having the at least one catalytically active surface region with a conical, pleated, cylindrical, frustoconical, frusto-pyramidal, spherical or hemispherical geometric form or is hedgehog-shaped. The surface of the at least one air purifying unit effective for the air purification can be increased by this shaping. However, the actual form of the surface leads to only a small increase in air resistance opposing the air flow in the housing.

Further, it is provided that the at least one lighting unit has the form of a circuitboard comprising a plurality of light-emitting diodes arranged in rows and at an equidistant spacing from one another. Through the arrangement of a plurality of light-emitting diodes it is achieved that almost the entire surface of the at least one air purifying unit is acted on by light and the light distribution is almost uniform in the housing.

However, the spacing does not have to be selected to be equidistant. The distribution of the light sources can also be different. Uniform irradiation of the surface must, however, always be ensured so as to achieve a cleaning effect which is as satisfactory as possible.

Moreover, it is provided that the circuitboard has a plurality of rows of light-emitting diodes on the upper side and the lower side. The circuitboard, if it is arranged centrally in the housing, can thereby illuminate both housing halves.

Finally, it is provided that air guide elements which deflect the air flow to the at least one photocatalytically active surface region of the at least one air purifying unit are arranged in the housing. In addition, a desired swirling of the air is thereby created. A particularly high level of cleaning performance is thus achieved.

In an advantageous embodiment of the invention it is provided that the air guide elements are arranged on the upper side and the lower side of the circuitboard. This simplifies the production process, the number of individual parts and the assembly of the device.

In an advantageous embodiment of the invention it is provided that the air purifying unit is arranged in or at the air intake of the air circulation flap of a motor vehicle. In this case, an individual air vent for the air purification device is not needed, since the air flow of the air circulation operation is utilised and conjunctively exploited.

In an advantageous embodiment of the invention it is provided that a VOC sensor for need-based control of the air purification device is arranged therein or that a $CO_2$ sensor already present in the motor vehicle is incorporated for need-based control of the air purification device.

BRIEF DESCRIPTION OF THE DRAWINGS

The air purification device according to the invention is described in the following on the basis of actual embodiments in the figures. The following description on the basis of the actual embodiments does not represent limitation of the invention to any of these actual embodiments.

In the figures:

FIG. 4 shows an air purification device with housing opened at the side;

FIG. 5 shows a perspective illustration of an air purification device with housing opened at the side;

FIG. 9 shows a lighting unit.

The same parts and/or components are provided with the same reference numerals in the figures. These parts and/or components substantially correspond with one another insofar as nothing to the contrary is indicated.

Figure 1:
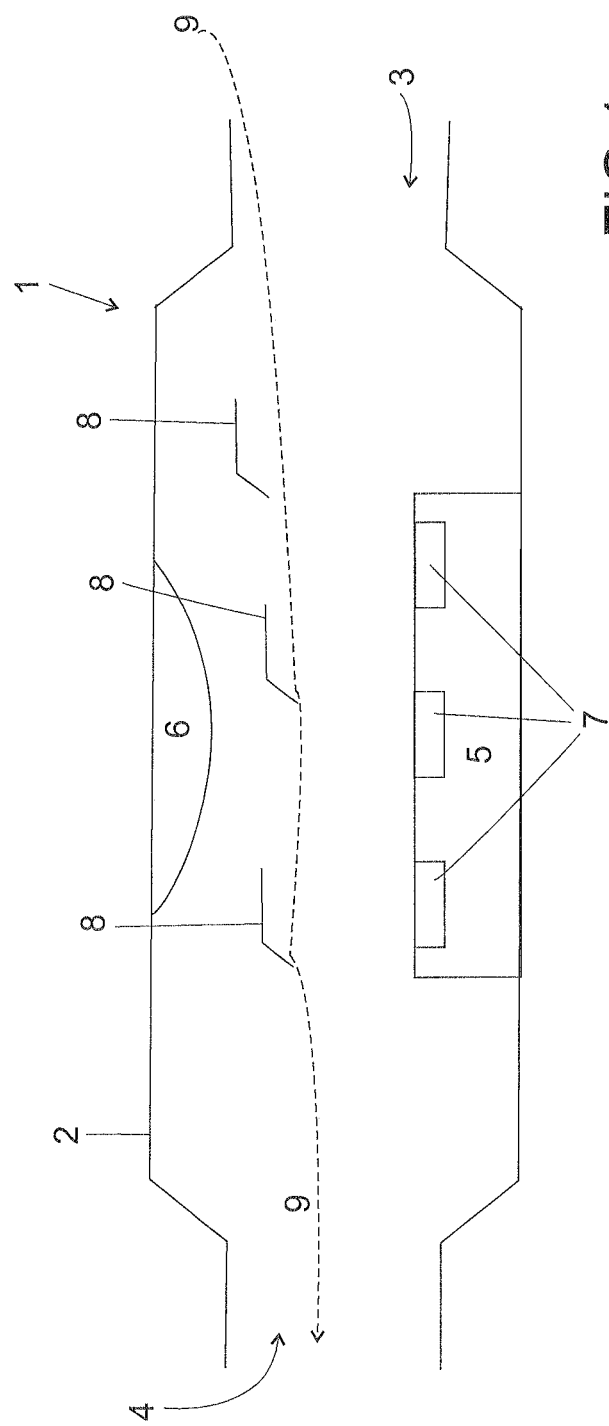
FIG. 1 shows a schematic construction of an air purification device according to the invention.

A section through a schematic air purification device 1 is illustrated in FIG. 1. The air purification device 1 has a housing 2. The shape of the housing 2 can have a round, oval, hexagonal, polygonal or, preferably, rectangular cross-section.

Design of the cross-section of the housing 2 in a rectangular form has proved particularly advantageous. The housing 2 is block-shaped.

The housing 2 preferably consists of plastics material; in a special embodiment, the selected plastics material is ABS.

The housing 2 has, at two mutually opposite ends, an inlet opening in the form of an air inlet channel 3 and an outlet opening in the form of an air outlet channel 4 for air supplied to the housing 2 by way of the air inlet channel 3.

Air to be purified is supplied by way of the air inlet channel 3 to the air purification device 1 into the housing 2 thereof; the air purified in the air purification device 1 is conducted out of the housing 2 again by way of the air outlet channel 4.

An air flow 9 forms in the housing 2. The air flow 9 runs through the housing 2 from the air inlet channel 3 to the air outlet channel 4. The air flow is directed in the housing 2.

An air purifying unit 5 is arranged in the housing 2. A plurality of air purifying units 5 can be arranged in the housing 2.

The air purifying unit 5 is arranged at one of the inner walls of the housing 2 and is mechanically positively or frictionally connectible with the inner wall. For that purpose, clips or mounts which fix the air purifying unit 5 to the inner wall of the housing 2 are provided.

A lighting unit 6 is arranged on the inner wall of the housing 2 to be opposite the air purifying unit 5. However, a plurality of lighting units 6 can also be arranged in the housing 2.

The lighting unit 6 is so arranged at the inner wall of the housing 2 that the light emitted by the lighting unit 6 is delivered so as to be directed almost entirely onto the air purifying unit 5.

In an advantageous embodiment of the invention lenses which focus the light of the lighting unit 6 onto the air purifying unit 5 are arranged in front of the lighting unit 6.

In a further embodiment of the invention prisms or mirrors which prevent the delivered light of the lighting unit 6 from not impinging on the air purifying unit 5 are arranged at the lighting unit 6.

In a further advantageous embodiment of the invention the interior of the housing 2 is painted white or provided with a light-reflecting surface coating.

The air purifying unit 5 has at least one photocatalytically active region 7. In the embodiment according to FIG. 1 three regions 7 of that kind are present.

The photocatalytically active regions 7 consist of titanium dioxide, i.e. $TiO_2$, or are doped with titanium dioxide ions, i.e. $TiO_2$ ions. However, use can also be made of other photocatalytically active materials.

The lighting unit 6 is now tailored to the photocatalytically active regions 7. The lighting unit 6 delivers ultraviolet light or visible light with a presettable or preset wavelength. The photons with the corresponding wavelength of the ultraviolet light or visible light of the lighting unit 6 when impinging on the photocatalytically active region 7 trigger a photochemical reaction in the titanium oxide which has the consequence that odiferous particles and/or noxious particles in the air are converted or destroyed. The odiferous particles and/or noxious particles impinging on the photocatalytically active regions 7 are destroyed or converted by the photochemical process and the supplied air is thus purified.

The lighting unit 6 is preferably at least one light-emitting diode, preferably a UV light-emitting diode. UV has the meaning ultraviolet.

In an advantageous embodiment of the invention a plurality of UV light-emitting diodes is present and forms the lighting unit 6. The light-emitting diodes are arranged with respect to one another in a row to be equidistant. Several rows of UV light-emitting diodes are then arranged in parallel adjacent to one another and at the same spacing from one another.

The lighting unit 6 is controlled by way of a control unit, which is not illustrated in FIG. 1.

Air guide elements 8 are arranged in the housing 2. These serve the purpose of guiding the air flow 9 in the housing 2 onto the air purifying unit 5 and the photocatalytically active regions 7 so that a largest possible part of the air flow 9 with the noxious particles and/or harmful substance particles passes to the photocatalytically active region 7 so as to photocatalytically react there. In order achieve a best possible flow of air around the photocatalytically active regions 7 of the air purifying unit 5 and at the same time to not impair the light delivery of the lighting unit 6 to the air purifying unit 5 the air guide elements 8 are arranged not above the photocatalytically active regions 7 of the air purifying unit 5, but before and after the lighting unit 6.

On incidence of ultraviolet light radiated by the lighting unit 6 the throughflowing air is correspondingly purified by the purifying unit 5 and the photocatalytically active regions 7 thereof.

Figure 2:
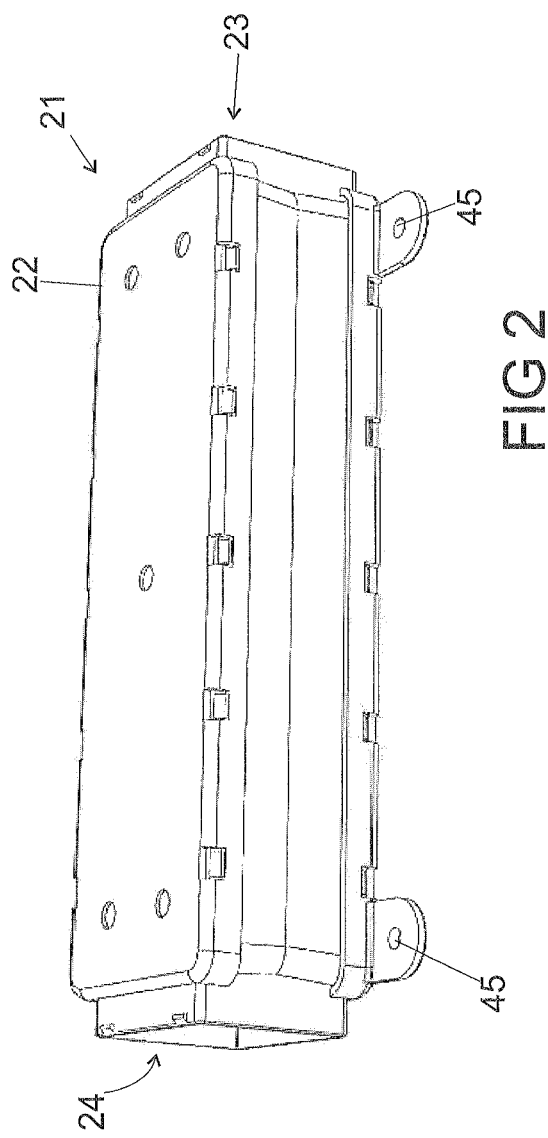
FIG. 2 shows a perspective view of an air purification device.

A housing 22 of a further embodiment of a further air purifying device 21 is illustrated in FIG. 2. The housing 21 consists of a plurality of individual parts which can be assembled to form the housing 22. The housing 22 is of block-shaped form and has towards one side a narrowed portion which goes over into the air inlet channel 23. Provided on the side of the housing 22 opposite the air inlet channel 23 is a further corresponding narrowed portion which forms the air outlet channel 24. The air to be purified is removed from the motor vehicle interior space, in particular sucked therefrom, and supplied by way of the air inlet channel 23 to the housing 22 and thus the air purifying device 21. Purification of the air then takes place in the housing 22 in a manner analogous to that described for FIG. 1 and the purified air is then discharged by way of the air outlet channel 24 and fed back to the vehicle interior space.

In addition, mounts 45 which are fixedly connected with the housing 22 are present at the housing. These mounts 45 serve the purpose of being able to secure the air purification device 21 in a motor vehicle at an intended location. For that purpose, a clamping connection or a screw-connection is provided.

Figure 3:
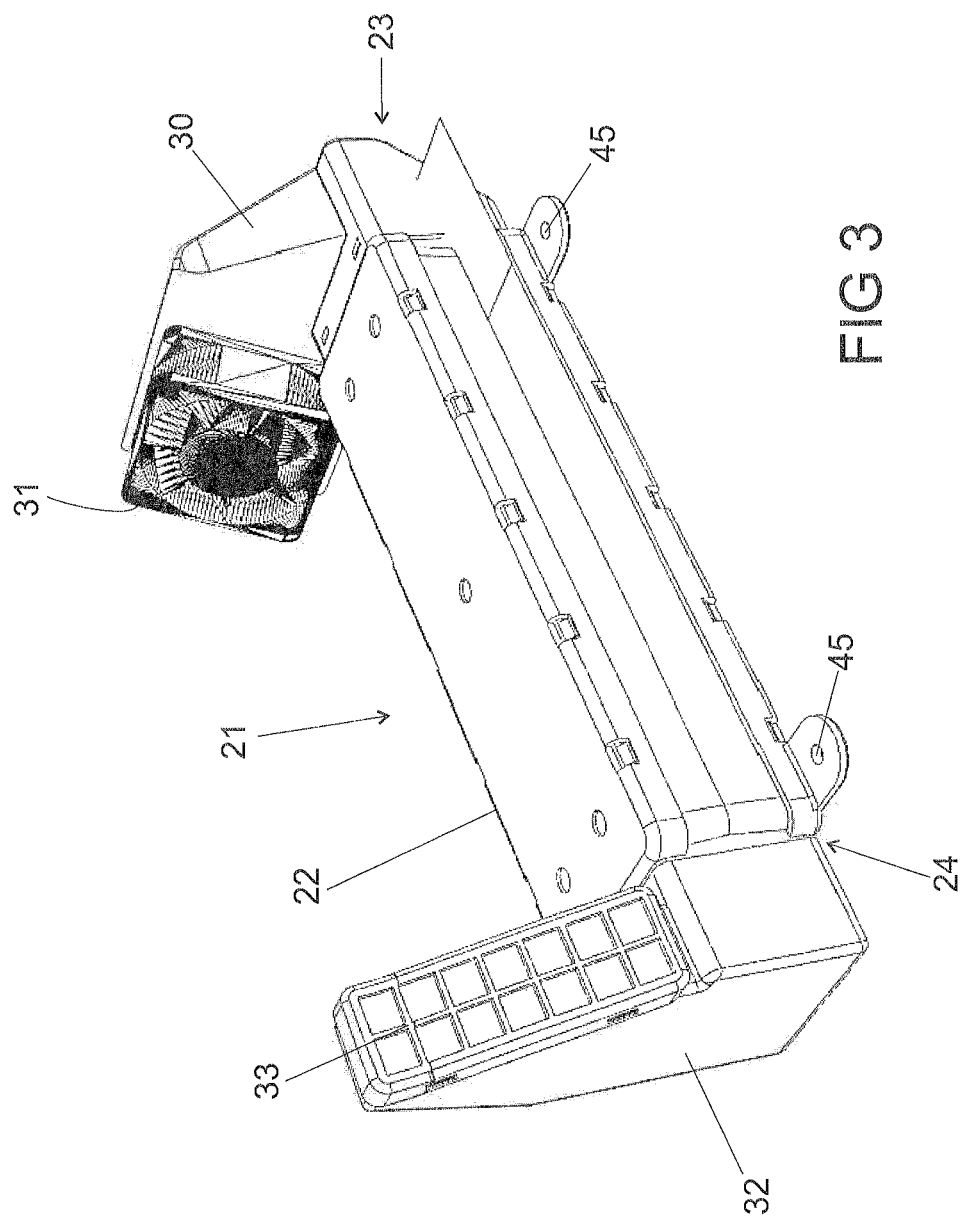
FIG. 3 shows a view of an air purification device according to the invention with the further relevant components.

The air purification device 21 with the housing 22 is illustrated in FIG. 3. Arranged at the air inlet channel 23 is an air feed channel 30, at the inlet of which a fan 31 is arranged which sucks the air out of the vehicle interior space and blows it through the air feed channel 30 and via the air inlet channel 23 into the housing 22 of the air purification device 21. The air feed channel 30 is plugged onto the narrowing of the air inlet channel 23 and is mechanically positively connected therewith.

In a special embodiment of the invention the air feed channel is connectible with the air inlet channel 23 or the housing 22 by means of a snap connection. Arranged on the side of the air outlet opening 24 is an air guide channel 32 which receives the outflowing air from the air outlet opening 24, channels the air and correspondingly feeds it back to the interior space of a motor vehicle from which the air was sucked by means of the fan (31).

In a further advantageous embodiment of the invention it is provided that at least one air filter unit 33 such as, for example, an HEPA filter or another form of air filter is arranged in the air guide channel 32.

The housing 22 of the air purification device 21 is illustrated opened at the side in FIG. 4. The relevant components which are arranged in the housing 22 are illustrated.

The air, which is to be purified, in the form of an air flow 29 is fed to the housing 22 by way of the air inlet channel 23 and the purified air in the form of the air flow 29 is conducted out of the housing 22 by way of the air outlet channel 24.

The housing 22 has a housing base 34 and a housing cover 35, which together with the housing side parts (not illustrated in FIG. 4) form the housing 22. The mounts 45 are arranged at the housing base 34. Both the housing base 34 and the housing cover 35 have, laterally at the outer side, a plurality of indentations 36 into which corresponding lugs at the housing side parts snap and thus connect the housing base 34 and the housing cover 35 by way of the housing side parts.

A respective air purifying unit 25 is arranged on the inner side of the housing cover 35 and the inner side of the housing base 34. An air purifying unit 25 extends almost over the entire area of the housing base 34 or the housing cover 35. Each air purifying unit 25 is mechanically positively and/or frictionally connected with the housing base 34 or the housing cover 35. This connection is effected by way of, for example, clipping, glueing or screw-connecting.

Each of the two air purifying units 25, i.e. one in the housing cover 35 and one at the housing base 34, is now optimised in its shape—as illustrated in FIG. 5—on the one hand to have a largest possible surface and on the other hand to provide least possible flow resistance to the air flow 29 in the housing 22. The pressure loss in the housing 22 is thus kept as small as possible, but at the same time the air flow 29 is conducted past a largest possible surface of the two air purifying units 25 and brought into contact therewith.

Pyramidal shapes 37 with a square or polygonal plan are illustrated in the concrete embodiment according to FIG. 4. These also appear like teeth which project upwardly from the housing base 34 or hang down from the housing cover 35. These pyramidal shapes 37 are respectively arranged equidistantly from one another.

In a particularly advantageous embodiment of the invention it is provided that the surface of the air purifying unit 35, which is coated or partly coated with titanium dioxide ($TiO_2$) or doped with titanium dioxide ions ($TiO_2$ ions), is designed in the form of a conical, pleated, cylindrical, frusto-conical, frusto-pyramidal, spherical or hemispherical geometric shape, or is hedgehog-shaped.

The air purifying unit 25 with the pyramidal shapes 37 is now advantageously doped with titanium dioxide ions, i.e. $TiO_2$ ions, or coated with titanium dioxide, i.e. $TiO_2$. This takes place preferentially in the region of the pyramidal shapes 37.

In a further embodiment of the invention it is provided that at least part regions of the air purifying unit 25 are doped with titanium oxide ions or partly coated or completely coated with titanium oxide.

It is now possible through the selected pyramidal shapes 37 that the air flow 29 flowing through the housing 22 flows around these pyramidal shapes 37 of the air purifying units 25 and thus the air purifying unit 25 has a largest possible photocatalytically active area.

A circuitboard 38 is arranged centrally in the housing 22. Light-emitting diode rows 39 with several light-emitting diodes 40, which are adjacent one another in a row and almost equidistant from one another, are now arranged on the upper side of the circuitboard 38 and the lower side of the circuitboard 38. The light-emitting diodes 40 are preferably light-emitting diodes which emit ultraviolet light.

The light-emitting diodes 40 arranged in the light-emitting diode rows 39 form the lighting unit 26, which serves the purpose of triggering the photocatalytic reaction. The photocatalytic process is set in motion by the ultraviolet light of the light-emitting diodes 40, which radiates in the direction of the pyramidal shapes 37 of the air purifying unit 25.

The air flow 29 flowing past is photocatalytically purified.

In the embodiment according to FIG. 4 the airflow 29 is divided up in the housing 22. In order to now bring the air flow 29 particularly satisfactorily into contact with the photocatalytically active regions of the air purifying units 25, air guide elements 28 are arranged on the circuitboard 38. These serve the purpose of guiding the air flow 29 to the photocatalytically active regions.

FIG. 5 shows a perspective illustration of FIG. 4. The embodiment of the form of the air purifying unit 25 with the design of pyramidal shapes 37 can be clearly seen, as also the arrangement of light-emitting diodes 40 in light-emitting diode rows 39 and the air guide elements 28 arranged on the circuitboard 38. In addition, supports 41 are present, which protrude in the direction of the circuitboard 38 from the air purifying units 25 attached to the housing base 34 or housing cover 35. These supports can be arranged at the housing base 34 or housing cover 35; the circuitboard 38 is fixable in cut-outs provided for that purpose and on these supports 39. The circuitboard 38 is arranged approximately centrally in the housing 22 and has an almost identical spacing from the housing base 34 and the housing cover 35.

Figure 6:
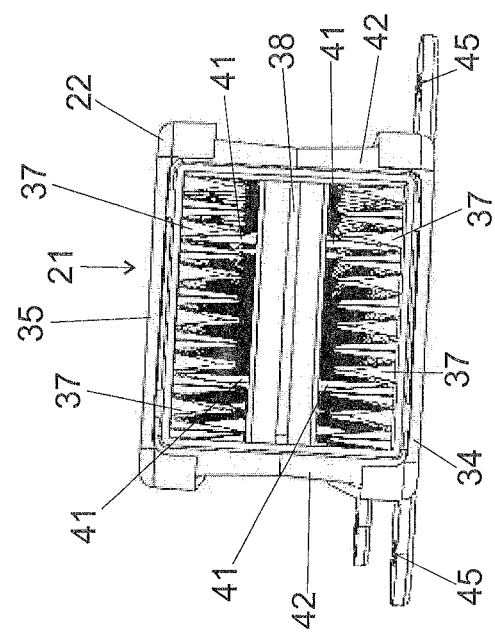
FIG. 6 shows a view into the air inlet channel of the air purification device.

A plan view of the air guide channel 23 is illustrated in FIG. 6. The supports 41 which fix the circuitboard 38 in the housing 22 are evident. The housing side parts 42 are insertable into guides in the housing cover 35 and housing base 34 and are fixed by way of the indentations 36 through snapping into the same.

The mounts 45 serve for securing the air purifying device 1.

Figure 7:
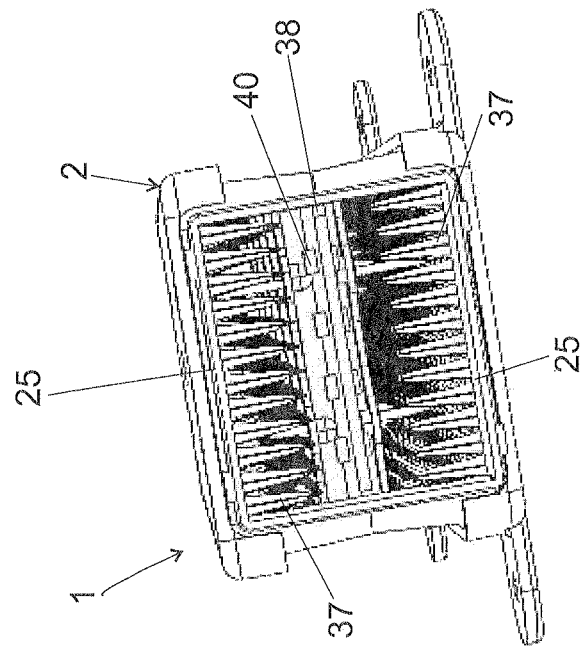
FIG. 7 shows a view into the air outlet channel of the air purification device.

A plan view of the air outlet channel 24 is illustrated in FIG. 7. The supports 41 which hold the circuitboard 38 centrally in the housing 22 are again present. Also illustrated are the arrangement of light-emitting diodes 40 on the circuitboard 38 and the shaping of the air purifying units 25 and the surface thereof, which is designed for purifying the air and for optimising air resistance, by means of pyramidal shapes 37.

Figure 8:
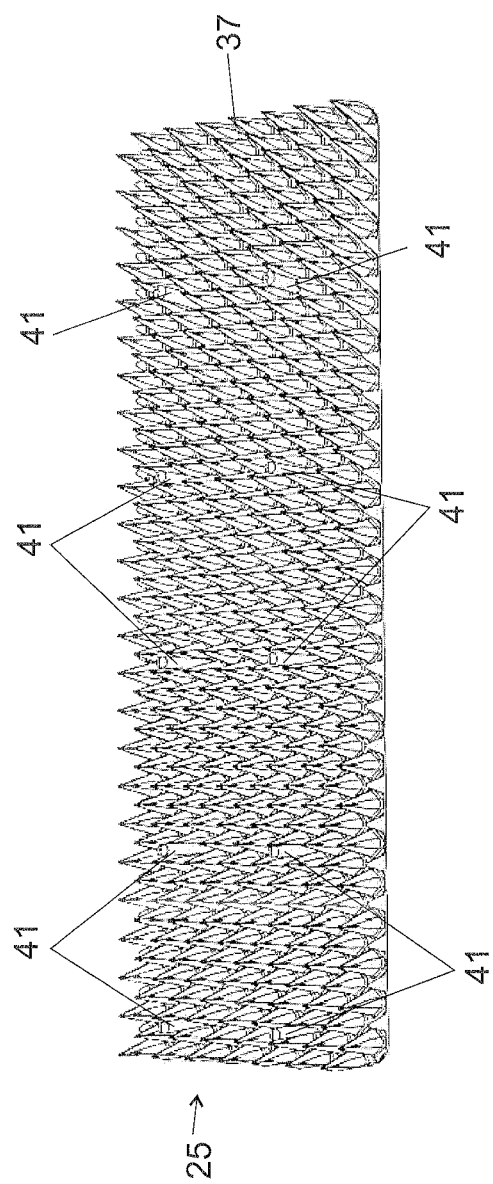
FIG. 8 shows a purifying unit.

An air purifying unit 25 with the surface design in the form of pyramidal shapes 37 is now illustrated in FIG. 8. The photocatalytically active regions of the pyramidal shapes 37 are produced in that the surface of the air purifying unit is initially produced from plastics material by a known and established production method and subsequently the surface is coated with a titanium oxide ($TiO_2$) in powder form. For that purpose, use can be made of the resin process. However, there is also the possibility of coating the surface by way of a SOL gel method. Moreover, use can be made of doped $TiO_2$ which on the one hand has a higher level of efficiency when irradiated with UV and on the other hand has been varied by introduction of molecules in such a way that a high level of activity is present even with visible light. In addition, the catalyser can already be included in the plastics material ($TiO_2$-doped plastics material) and burnt free. There is the possibility of vapour deposition or powder coating. In addition, there is the possibility of using other photocatalysers such as $LiNbO_3$.

Through the concrete design of the surface with pyramidal shapes 37 there is created, for a base area of the air purifying unit 25 of 117 square centimetres, a surface of approximately 521 square centimetres, i.e. the surface of the air purifying unit 25 is greater than the base area by almost the factor five.

As a result, a large area with photocatalytically active regions can be created by the coating with titanium dioxide ($TiO_2$).

The supports 41 are integrated as a component of the air purifying unit 25. In the case of coating or doping with titanium dioxide ($TiO_2$) the supports 41 similarly act as photocatalytically active regions.

The circuitboard 38 is illustrated in a plan view in FIG. 9. The non-visible lower side is of analogous form. The circuitboard 38 has four light-emitting diodes 40 respectively arranged in rows 39. In total, five light-emitting diode rows 39 are present respectively on the upper side and lower side of the circuitboard 38. The air guide elements 28 are also illustrated.

The light-emitting diodes 40 are light-emitting diodes emitting ultraviolet light, which is preferably tailored to the titanium dioxide and to the photocatalytic action thereby able to be produced and which has a wavelength in the region of visible light between 400 and 500 nanometres, preferably in the region around 450 nanometres. In the case of use of doped $TiO_2$, use should be made of UV-A light, preferably with a 367 nm wavelength.

REFERENCE NUMERAL LIST 1, 21 air purification device
2, 22 housing
3, 23 air inlet channel
4, 24 air outlet channel
5, 25 air purifying unit
6, 26 lighting unit
7, 27 photocatalytically active region of the air purifying unit
8, 28 air guide elements
9, 29 air flow
30 air feed channel
31 fan
32 air guide channel
33 air filter unit
34 housing base
35 housing cover
36 indentions
37 pyramidal shapes
38 circuitboard
39 light-emitting diode rows
40 light-emitting diodes
41 supports
42 housing side parts
45 mounts

The invention claimed is:

1. An air purification device, comprising a housing having at least one inlet opening for supply of an air flow and at least one outlet opening for discharge of the air flow supplied by way of the at least one inlet opening, wherein at least one air purifying unit and at least one lighting unit are arranged in the housing, wherein the at least one air purifying unit and the at least one lighting unit are arranged opposite one another in the housing, the at least one air purifying unit has at least one photocatalytically active surface region and the air flow is guided in the housing at least partially along the at least one photocatalytically active surface region of the at least one air purifying unit, wherein the at least one photocatalytically active surface region of the at least one air purifying unit can be irradiated with light by the at least one lighting unit and the at least one photocatalytically active surface region is coated at least partly with titanium dioxide or doped with titanium dioxide ions, wherein the at least one air purifying unit comprises two air purifying units arranged opposite one another at inner walls of the housing, wherein the at least one lighting unit is arranged in the housing in the center of the housing to traverse the housing in a plane so that the light emitted by the at least one lighting unit is incident almost in its entirety on the two air purifying units, wherein the at least one photocatalytically active surface region of each of the two air purifying units is shaped with a conical, pleated, cylindrical, frusto-conical, frusto-pyramidal, spherical or hemispherical geometric form or is spiny and the at least one lighting unit is formed as a circuit board, wherein a plurality of light-emitting diodes are arranged in rows and at an equidistant spacing from one another on the circuit board, wherein the rows of the plurality of light-emitting diodes are arranged on an upper side and on a lower side of the circuit board, and wherein air guide elements arranged in the housing and comprising deflectors protruding from the circuit board in an air channel of the housing between the at least one inlet opening and the at least one outlet opening, so that the air flow in the air channel is deflected onto the at least one photocatalytically active surface region of the at least one air purifying unit.

2. The air purification device according to claim 1, further comprising lenses which focus the light emitted by the at least one lighting unit on the at least one air purifying unit and are arranged in front of the at least one lighting unit or light reflectors or light-reflecting regions which reflect the light emitted by the at least one lighting unit in the direction of the at least one air purifying unit and are arranged behind and/or adjacent to the at least one lighting unit.

3. The air purification device according to claim 2, wherein at least one inner wall of the housing is painted white and/or coated with a light-reflecting material.

4. The air purification device according to claim 2, wherein the plurality of light-emitting diodes of the at least one lighting unit comprise at least one light-emitting diode which emits ultraviolet light.

5. The air purification device according to claim 2, wherein the at least one air purifying unit extends over almost the entire area of a housing base and/or a housing cover of the housing and is fixable to the housing base and/or housing cover.

6. The air purification device according to claim 2, wherein the air purification device is arranged in or at an air intake of an air circulation flap of a motor vehicle.

7. The air purification device according to claim 1, wherein at least one inner wall of the housing is painted white and/or coated with a light-reflecting material.

8. The air purification device according to claim 7, wherein the plurality of light-emitting diodes of the at least one lighting unit comprise at least one light-emitting diode which emits ultraviolet light.

9. The air purification device according to claim 7, wherein the at least one air purifying unit extends over almost the entire area of a housing base and/or a housing cover of the housing and is fixable to the housing base and/or housing cover.

10. The air purification device according to claim 7, wherein the air purification device is arranged in or at an air intake of an air circulation flap of a motor vehicle.

11. The air purification device according to claim 1, wherein the plurality of light-emitting diodes of the at least one lighting unit comprise at least one light-emitting diode which emits ultraviolet light.

12. The air purification device according to claim 11, wherein the at least one air purifying unit extends over almost the entire area of a housing base and/or a housing cover of the housing and is fixable to the housing base and/or housing cover.

13. The air purification device according to claim 1, wherein the at least one air purifying unit extends over almost the entire area of a housing base and/or a housing cover of the housing and is fixable to the housing base and/or housing cover.

14. The air purification device according to claim 13, wherein the air purification device is arranged in or at an air intake of an air circulation flap of a motor vehicle.

15. The air purification device according to claim 1, wherein the air guide elements are arranged on the upper side and the lower side of the circuit board.

16. The air purification device according to claim 15, wherein the air purification device is arranged in or at an air intake of an air circulation flap of a motor vehicle.

17. The air purification device according to claim 1, wherein the air purification device is arranged in or at an air intake of an air circulation flap of a motor vehicle.

18. The air purification device according to claim 1, wherein a volatile organic compound sensor for need-based control of the air purification device is arranged therein or a $CO_2$ sensor already present in a motor vehicle is incorporated for need-based control of the air purification device.

\* \* \* \* \*

UNITED STATES PATENT AND TRADEMARK OFFICE
CERTIFICATE OF CORRECTION

PATENT NO. : 10,918,759 B2  
APPLICATION NO. : 16/061308  
DATED : February 16, 2021  
INVENTOR(S) : Fiedler et al.

Page 1 of 1

It is certified that error appears in the above-identified patent and that said Letters Patent is hereby corrected as shown below:

In the Claims

Claim 2, Column 10, Line 33, "unit or" should be --unit, or--.

Signed and Sealed this  
Twenty-fourth Day of September, 2024

Katherine Kelly Vidal  
*Director of the United States Patent and Trademark Office*